United States Patent
Kuro-o et al.

(10) Patent No.: US 7,537,903 B2
(45) Date of Patent: May 26, 2009

(54) FGF21 UPREGULATES EXPRESSION OF GLUT-1 IN A βKLOTHO-DEPENDENT MANNER

(75) Inventors: Makoto Kuro-o, Dallas, TX (US);
Yasushi Ogawa, Dallas, TX (US);
Hiroshi Kurosu, Dallas, TX (US);
Kevin Rosenblatt, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 4 days.

(21) Appl. No.: 12/107,895

(22) Filed: Apr. 23, 2008

(65) Prior Publication Data

US 2008/0261236 A1 Oct. 23, 2008

(51) Int. Cl.
*G01N 33/53* (2006.01)
(52) U.S. Cl. ...................................................... 435/7.2
(58) Field of Classification Search .................... None
See application file for complete search history.

(56) References Cited

OTHER PUBLICATIONS

Kurosu et al. (2006) J. Biol. Chem. 281: 6120-6123.*

* cited by examiner

*Primary Examiner*—Michael Pak
(74) *Attorney, Agent, or Firm*—Richard Aron Osman

(57) ABSTRACT

A method is provided to identify a modulator of βKlotho-dependant glucose transporter-1 (GLUT-1) upregulation that specifically modulates interaction of βKlotho and an FGFR.

1 Claim, No Drawings

FGF21 UPREGULATES EXPRESSION OF GLUT-1 IN A βKLOTHO-DEPENDENT MANNER

STATEMENT REGARDING FEDERALLY SPONSORED RESEARCH

This work was supported by Federal Grants from the National Institute on Aging (Contract Nos. R01 AG019712, and R01 AG025326). The U.S. government may have rights in any patent issuing on this application.

BACKGROUND OF THE INVENTION

The field of the invention is βKlotho-dependent GLUT-1 regulation.

Fibroblast growth factor 21 (FGF21) was identified based on cDNA sequence homology to other FGFs (1). Phylogenetic and structural analyses have assigned FGF21 to the FGF19 subfamily, which consists of FGF15 (the mouse ortholog of human FGF19), FGF19, FGF21, and FGF23 (2). The FGF19 subfamily members distinguish themselves from the other 15 FGFs in that they function in an endocrine fashion. FGF23 is secreted primarily from bone and acts on the kidney to inhibit phosphate reabsorption and vitamin D biosynthesis (3-5). FGF15 is expressed by intestinal epithelium and is involved in the negative feedback regulation of bile acid synthesis in the liver (6). FGF21 is expressed predominantly in the liver and has emerged as a metabolic regulator of glucose uptake in adipocytes during a search for novel agents with therapeutic potential to treat diabetes mellitus (7, US Pat Publ No. 20040259780). Administration of recombinant FGF21 lowered blood glucose levels in both obese mice and in diabetic mice. Furthermore, transgenic mice that overexpress FGF21 were hypoglycemic, sensitive to insulin, and resistant to diet-induced obesity (7).

FGF21 can activate FGF receptors (FGFRs) and signaling molecules downstream, including FGFR substrate 2α (FRS2α) and 44/42 MAP kinase (ERK1/2), in adipocytes (7-10). However, efforts to demonstrate a direct interaction between FGFRs and FGF21 have failed. In addition, various cell types of nonadipocyte origin including 3T3-L1 preadipocytes do not respond to FGF21 even though they express multiple FGFR isoforms (7). Furthermore, BaF3 cells that overexpress FGFRs require suprapharmacological doses of FGF21 (200-800 nM) to produce a detectable mitogenic response (8-10).

We and others identified Klotho, a single-pass transmembrane protein, as an essential cofactor for FGF23 to activate FGF23 signaling (11, 12). Klotho was originally identified as a gene mutated in the klotho mouse that exhibited phenotypes resembling human premature-aging syndromes (13). Major phenotypic overlaps were observed between Klotho-deficient mice and Fgf23 knockout mice (14, 15). It was determined that Klotho bound to multiple FGFRs and was necessary for FGF23 to bind FGFRs and activate FGF signaling in various types of cultured cells (11).

βKlotho was isolated based on cDNA sequence homology to Klotho (18). The βKlotho gene encodes a single-pass transmembrane protein that shares 41% amino acid identity with Klotho and in addition to adipose tissue is also expressed in liver and pancreas. Mice deficient in βKlotho have overlapping phenotypes with mice lacking FGF15 or FGFR4 (6, 19, 20). These phenotypes include increased bile acid synthesis and increased expression of two key bile acid syntheses, CYP7A1 and CYP8B1, in the liver.

SUMMARY OF THE INVENTION

The invention provides methods and compositions to identify a modulator of βKlotho-dependent glucose transporter-1 (GLUT-1) upregulation that specifically modulates interaction of βKlotho and an FGFR, and to modulate βKlotho-dependent glucose transporter-1 (GLUT-1) upregulation and interaction of βKlotho and an FGFR. In one embodiment, the method comprising steps: (a) contacting an agent with a βKlotho-dependent GLUT-1 assay system under conditions wherein but for the presence of the agent, the assay has a reference GLUT-1 readout; (b) detecting an agent-biased specific modulation of the GLUT-1 readout significantly different from the reference readout, indicating that the agent is a modulator of GLUT-1 upregulation; and (c) determining that the agent specifically modulates the interaction of the βKlotho and the FGFR, indicating that the modulation of the GLUT-1 upregulation is βKlotho-dependent.

In particular embodiments, the assay system (i) comprises cultured 3T3-L1 adipocytes, and the GLUT-1 readout is glucose uptake or glycerol release in the adipocytes; (ii) is a mouse, and the GLUT-1 readout is increased serum FFA or β-hydroxybutyrate; or (iii) is a transgenic mouse that overexpresses FGF21.

In another embodiment, the agent is an antibody. In another embodiment, the invention provides an antibody that specifically binds a βKlotho/FGFR complex, wherein the antibody modulates βKlotho-dependent GLUT-1 upregulation.

DETAILED DESCRIPTION OF SPECIFIC EMBODIMENTS OF THE INVENTION

In this work we show that βKlotho, a Klotho family protein, functions as the cofactor required for FGF21 signaling. Our invention provides methods to identify a modulator of βKlotho-dependent glucose transporter-1 (GLUT-1) upregulation that specifically modulates interaction of βKlotho and an FGFR. The invention further provides compositions that modulate βKlotho-dependent glucose transporter-1 (GLUT-1) upregulation and specifically, preferably directly, modulate interaction of βKlotho and an FGFR.

The method comprises steps: contacting an agent with a βKlotho-dependent GLUT-1 assay system under conditions wherein but for the presence of the agent, the assay has a reference GLUT-1 readout. The agent is a candidate pharmaceutical agent not previously known to modulate βKlotho-dependent glucose transporter-1 (GLUT-1) upregulation and specifically modulate interaction of βKlotho and an FGFR, and other than a native FGF19 subfamily ligand. Examples of agents that may be tested in method include compounds of a drug screening compound library, putative FGF21 protein mimetics, antibodies, etc.

The agent is contacted with the assay system according to the selected assay system and agent. For example, in an in vitro cell culture system the agent may be added directly to the cell culture medium, or the cells may be transfected with the agent, etc. In an in vivo system, such as a rodent model, the agent is contacted with the assay system by administering the agent to the animal such as by feeding, injection, topical administration, aerosol inhalation, or any other method suitable for the particular agent being tested.

The GLUT-1 assay system is βKlotho-dependent, requiring βKlotho for FGF21 signaling and activation of downstream ERK1/2 and upregulation of GLUT-1. The GLUT-1 readout may be a direct or indirect measurement of GLUT-1. An exemplary in vitro assay is the glucose uptake assay described in the Examples section, in which the readout is a direct measurement of GLUT1 protein levels in differentiated adipocytes. Alternatively, the readout may be GLUT1 mRNA levels. An exemplary in vivo system is the ob/ob mouse model of hyperglycemia (7). Other assay systems provide an indirect measurement of GLUT-1, such as a readout of glycerol or free fatty acid release in 3T3-L1 adipocytes (see e.g. Hong et al., Kaohsiung J Med Sci. (2002) 18:157-63; and Rudich et al, Diabetes. (2001) 50:1425-31), increased lipolysis and ketogenesis (serum free fatty acid and β-hydroxybutyrate) in mice, improved insulin sensitivity or blood glucose levels in ob/ob mice (7). The assay system may be genetically engineered to express one or more members of the βKlotho signaling pathway, e.g. FGF21, βKlotho, FGFR, ERK, etc. In one embodiment, the assay system is a transgenic mouse that over- or under-expresses FGF21. Agents that restore FGF signaling, or restore increased lipolysis and ketogenesis in these mice are identified as FGF21 or βKlotho agonists or antagonists, respectively.

An agent-biased specific modulation of the GLUT-1 readout significantly different from the reference readout is detected using suitable methodology, such as described below. Controls may include the presence or absence of FGF21 or βKlotho in the assay system. A significant difference (increase or decrease) between the reference readout and the agent-biased read-out indicates that the agent is a modulator (enhancer or inhibitor) of GLUT-1 upregulation.

The assay further comprises the step of determining that the agent specifically modulates interaction of βKlotho and an FGFR. This step can be performed either prior to or after the GLUT-1 assay. Agents that specifically modulate interaction of βKlotho and an FGFR may do so by specifically binding to a βKlotho-FGFR complex, thereby agonizing or antagonizing the interaction. A variety of interaction or binding assays can be used to determine that an agent specifically binds βKlotho-FGFR, such as the pull down assay described below.

Assays that measure activation of 44/42 MAP kinase (ERK1/2) can also be used to determine whether an agent specifically modulates interaction of βKlotho and an FGFR. An HEK293 cell line stably transfected with both a βKlotho expression vector and a reporter gene that expresses EGFP (or DsRed Express-1) under the control of the Egr-1 promoter containing an ERK-response element, will elicit a green (or red, respectively) fluorescence when ERK is activated, which can be quantified by fluorescence spectrophotometer in a high-throughput assay. This assay is used to identify agents that are FGF19 or FGF21 mimetics that activate ERK. As a control, an ERK-reporter cell line lacking βKlotho is used to identify agents that activate ERK independently of βKlotho which do not specifically modulates interaction of βKlotho and an FGFR. As another control, agents are identified that inhibit FGF2-induced ERK activation in the ERK-reporter cell line, which inhibit ERK independently of βKlotho.

Another aspect of the invention is an antibody that specifically binds, agonizes or antagonizes the βKlotho/FGFR complex, particularly wherein the antibody is a modulator of βKlotho-dependent GLUT-1 upregulation. Such antibodies are isolated in screens described herein. In one embodiment, screened antibody libraries are selected or generated for affinity to βKlotho, FGFR1c, or a βKlotho/FGFR complex. For example, βKlotho and/or FGFR are used as an immunogen to generate monoclonal antibodies which are screened for their ability to specifically bind βKlotho-FGFR and to specifically modulate βKlotho-dependent glucose transporter-1 (GLUT-1) upregulation. The invention also provides such antibodies in pharmaceutically-acceptable form, particularly in pharmaceutically-acceptable dosage form, such as formulated and/or dosed with a pharmaceutically-acceptable carrier or excipient.

EXAMPLES

FGF21 Requires βKlotho to Activate FGF Signaling. Neither FGF21 nor FGF23 signaled in parental 293 cells as evidenced by lack of induction of phosphorylation of FRS2α and ERK1/2. We previously reported that ectopic overexpression of Klotho conferred responsiveness to FGF23 on 293 cells (11). However, these Klotho-overexpressing cells did not respond to FGF21. In contrast, 293 cells expressing the related βKlotho protein acquired the ability to respond to FGF21.

βKlotho Binds to Multiple FGFRs. The mammalian FGFRs are encoded by four distinct genes (FGFR1-FGFR4). The ectodomain of prototypical FGFRs consists of three Ig-like domains (D1-D3). A major alternative mRNA splicing event within the D3 of FGFR1-3 generates "b" and "c" isoforms, which have distinct FGF-binding specificities. An additional splicing event generates shorter FGFR1-3 isoforms lacking D1 and/or D1-D2 linker (9). We transiently expressed different FGFR isoforms and βKlotho in 293 cells and performed coimmunoprecipitation experiments. FGFR1c and FGFR4 precipitated βKlotho more efficiently than the other FGFRs. In contrast, the FGFR b isoforms did not pull down βKlotho under these experimental conditions.

Consistent with the strong interaction between βKlotho and FGFR1c and 4, βKlotho-FGFR1c and βKlotho-FGFR4 complexes were able to pull down FGF21 more efficiently than FGFRs alone and the other βKlotho-FGFR combinations, demonstrating that FGF21 requires βKlotho to bind to its cognate FGFRs stably.

FGF21 Activity Depends on βKlotho Expression in Adipocytes. Because FGF21 stimulates glucose uptake in differentiated adipocytes but not in preadipocytes (7), we reasoned that differentiated adipocytes and not preadipocytes express βKlotho. Indeed, we detected no expression of βKlotho in preadipocytes, and furthermore, FGF21 failed to elicit a signal in these cells. The differentiated adipocytes, however, expressed βKlotho abundantly and responded robustly to FGF21. To further document the dependence of FGF21 on βKlotho, we followed βKlotho expression as preadipocytes differentiated into adipocytes. Expression of βKlotho was detected as early as day 4 and continued to increase up to day 10. This temporal increase in βKlotho expression correlated with the ability of FGF21 to induce phosphorylation of FRS2α and ERK1/2. We also studied time course and dose response of FGF21-induced phosphorylation of FRS2α and ERK1/2. Phosphorylation of FRS2α and ERK1/2 became evident at 3 and 5 min, respectively, and began to decline at ~60 min after cell stimulation. Activation of FGF signaling was detectable with as low as 10 ng/ml (0.3 nM) FGF21 and saturated at 1,000 ng/ml (30 nM) FGF21. Lastly, we showed that endogenous βKlotho was able to pull down endogenous FGFR1c in differentiated adipocytes, indicating that βKlotho and FGFR1c form a complex under physiological conditions.

We knocked down βKlotho expression in differentiated adipocytes by using an siRNA approach. Four independent siRNAs against different sequences in βKlotho suppressed activation of both FRS2α and ERK1/2 by FGF21 and more importantly, abolished the effect of FGF21 on glucose uptake, indicating that βKlotho is essential for FGF21 to exert its metabolic activity on adipocytes.

FGF21-induced glucose uptake in adipocytes is accompanied by up-regulation of glucose transporter 1 (GLUT1), which is known to regulate insulin-independent glucose uptake, but not glucose transporter 4 (GLUT4), which primarily contributes to insulin-dependent glucose uptake (7, 16). Therefore, we determined GLUT1 and GLUT4 protein levels and found that the knockdown of βKlotho expression by siRNA also attenuated the ability of FGF21 to increase GLUT1 expression, indicating that FGF21-βKlotho signaling is an important regulator in insulin-independent glucose uptake in adipocytes.

The effect of FGF21 on glucose uptake becomes evident several hours after the stimulation and lasts for 24 h or longer (7) even though FGF21-induced Akt phosphorylation diminishes within 30 min in 3T3-L1 adipocytes (17). In contrast, insulin-induced glucose uptake becomes evident within minutes after stimulation in these cells and attenuates within hours. We conclude that the prolonged effect of FGF21 influences glucose metabolism under physiological settings. In fact, FGF21 has a potent and sustained blood glucose-lowering effect when administered into diabetic and obese mice (7). These observations indicate that FGF21 and insulin play distinct roles in the regulation of glucose metabolism: FGF21 induces a moderate and sustained increase in glucose uptake primarily through up-regulating GLUT1 expression, whereas insulin induces a strong and transient increase through promoting GLUT4 translocation from the intracellular pool to the plasma membrane.

To determine the dependence of FGF21 signaling on βKlotho in an in vivo setting, we injected FGF21 into mice and analyzed ERK1/2 phosphorylation in white adipose tissue (WAT), skeletal muscle, and kidney. βKlotho was expressed in WAT but not in the skeletal muscle or kidney. Consistent with the expression pattern of βKlotho, FGF21 induced ERK1/2 phosphorylation only in WAT. As a control, injection of FGF23 into mice stimulated ERK1/2 phosphorylation only in the kidney where Klotho is expressed. These data evidence the requirement of βKlotho and Klotho in FGF21- and FGF23-mediated tissue response, respectively.

Expression Vectors. Expression vectors for mouse FGFRs with a V5 epitope tag at the C terminus and murine FGF23 (R179Q) were described previously (11). The murine βKlotho cDNA was obtained by reverse transcriptase PCR from mRNAs of differentiated 3T3-L1 adipocytes. cDNA encoding murine FGF21 (IMAGE Clone; Invitrogen, Carlsbad, Calif.) or murine βKlotho was cloned into pEF1 expression vector (Invitrogen). Before subcloning, a FLAG epitope tag was added to the C terminus of βKlotho, and appropriate restriction enzyme sites were added to both ends by using synthetic oligonucleotides and PCR.

Cell Culture. 3T3-L1 preadipocytes (American Type Culture Collection, Rockville, Md.) were maintained in DMEM containing 10% calf serum (Mediatech, Herndon, Va.). Differentiation to adipocytes was induced by culturing the cells for 2 days in differentiation medium [DMEM (American Type Culture Collection)/10% FBS/10 mM Hepes/MEM nonessential amino acids (NEAA)/penicillin/streptomycin (PC/SM) (all from Invitrogen)/2 μM insulin/1 μM dexamethasone/0.25 mM 3-isobutyl-1-methylxanthine (IBMX) (all from Sigma-Aldrich, St. Louis, Mo.)] and then culturing in differentiation medium without dexamethasone and IBMX for another 2 days. Thereafter, the medium was changed every 2 days with DMEM supplemented with 10% FBS/10 mM Hepes/NEAA/PC/SM. Accumulation of lipid droplets was observed in >95% of cells after 7 days, and the cells at day 7-10 were used for experiments.

Preparation of FGF21 and FGF23. Human recombinant FGF21 and FGF23 (R179Q) were expressed in Escherichia coli, refolded in vitro, and purified by affinity, ion-exchange, and size-exclusion chromatographies following a previously published protocol (21). Serum-free conditioned medium containing murine FGF21 was collected from 293 cells transiently transfected with the FGF21 expression vector. The activity of FGF21 in the cell culture medium was determined by comparing its ability to induce ERK1/2 phosphorylation in differentiated 3T3-L1 adipocytes with that of recombinant human FGF21 of known concentration. The activity of murine FGF23 (R179Q) present in the cell culture medium was determined by using 293 cells stably expressing Klotho as described previously (11). Conditioned medium with activity equivalent to that of 2,000 ng/ml (67 nM) recombinant human FGF21 and 300 ng/ml (10 nM) FGF23, respectively, was used to stimulate cultured cells. The same amount of serum-free conditioned medium from mock-transfected 293 cells was used as a negative control.

Immunoprecipitation and Immunoblotting. Subconfluent 293 cells were transfected with expression vectors for βKlotho and FGFRs 36 h before the experiments by using Lipofectamine as carrier (Invitrogen). The cells were lysed in buffer containing inhibitors for phosphatase and proteinase as described previously (22). After saving a portion of each cell lysate sample for immunoblotting with anti-βKlotho antibody, the cell lysates were incubated with anti-V5-agarose beads (Sigma-Aldrich) at 4° C. for 3 h. The beads were washed four times with Tris-buffered saline containing 1% Triton X-100 (TBST); bead-bound proteins were eluted with Laemmli sample buffer, electrophoresed, and then transferred to Hybond C Extra membrane (Amersham Biosciences, Piscataway, N.J.). The protein blots were incubated with anti-βKlotho antibody (R&D Systems, Minneapolis, Minn.) or anti-V5 antibody (Invitrogen) followed by horseradish peroxidase-conjugated anti-goat IgG (Santa Cruz Biotechnology, Santa Cruz, Calif.) or anti-mouse IgG (Amersham Biosciences). Chemiluminescence signals were developed with the SuperSignal West Dura system (Pierce, Rockford, Ill.). For detection of endogenous interaction between βKlotho and FGFR1c in differentiated 3T3-L1 adipocytes, cell lysate samples were incubated with anti-FGFR1c antibody (Santa Cruz Biotechnology) and protein G-Sepharose at 4° C. for 2 h. The Sepharose beads were washed four times with complete lysis buffer and then twice with lysis buffer lacking Triton X-100. Bead-bound proteins were eluted with Laemmli sample buffer and subjected to immunoblot analysis by using anti-βKlotho or anti-FGFR1c antibody.

FGF21 Pull-Down Experiments. Cell lysate samples prepared from 293 cells transfected with FGFR alone or from 293 cells cotransfected with FGFR and βKlotho were incubated with anti-V5-agarose beads at 4° C. for 3 h. The beads were washed four times with TBST and then incubated with serum-free conditioned medium containing murine FGF21 at 4° C. for 3 h. Thereafter, the beads were washed three times with Krebs-Ringer-Hepes buffer (118 mM NaCl/4.96 mM KCl/2.54 mM $CaCl_2$/1.19 mM $KH_2PO4$/1.19 mM $MgSO_4$/20 mM Hepes, pH 7.4) containing 1% Triton X-100 followed by three washes with the same buffer lacking Triton X-100. Bead-bound proteins were eluted with Laemmli sample buffer and subjected to immunoblot analysis by using anti-V5 antibody, anti-βKlotho antibody, or anti-mouse FGF21 antibody (R&D Systems).

Immunoblot Analysis of FGF Signaling. Cells cultured on multiwell plates were serum-starved overnight and then treated for 10 min either with human recombinant FGF21 or FGF23 (R179Q) or FGF1 (FGF1 was from Upstate Biotechnology, Lake Placid, N.Y.). The cells were snap-frozen in liquid nitrogen and processed for immunoblot analysis by using anti-phospho-FRS2α antibody (Cell Signaling Technology, Beverly, Mass.), anti-phospho-44/42 MAP kinase (ERK1/2) antibody (Cell Signaling Technology), and anti-ERK antibody (Cell Signaling Technology) as described previously. Wild-type, 8-week-old, male inbred 129sv mice were administered either human recombinant FGF21 (0.3 μg g$^{-1}$ body weight) or FGF23 (R179Q, 0.1 μg g$^{-1}$ body weight) or vehicle (10 mM Hepes, pH 7.4/150 mM NaCl) by injection into the inferior vena cava. Perigonadal fat pads, kidneys, and hind limb muscles were excised 15, 17, and 19 min, respectively, after protein injection. The tissues were flash-frozen in liquid nitrogen and processed for immunoblot analysis by using anti-phospho-ERK, anti-ERK, and anti-actin (Chemicon International, Temecula, Calif.) antibodies.

Knockdown of βKlotho by RNA Interference. 3T3-L1 adipocytes were transfected with siRNA duplexes by electroporation as described previously (23). Briefly, differentiated 3T3-L1 adipocytes were harvested by using 0.5 mg/ml collagenase (Sigma-Aldrich), washed twice with PBS, and suspended in PBS (2×10$^7$ per ml). The cells were mixed with 5 nmol per 10$^7$ cells of siRNA oligonucleotide against four different sequences in βKlotho or nontargeting randomized sequences and electroporated with a gene pulser system at the setting of 0.18 kV and 960 μF capacitance (Bio-Rad, Hercules, Calif.). Immediately after electroporation, the cells were mixed with complete medium and incubated for 10 min before reseeding onto collagen I-coated 12-well plates (Becton Dickinson Labware, Bedford, Mass.). Thirty to forty hours after transfection, the cells were serum-starved overnight and then stimulated with FGF21 or FGF1 and assayed for phosphorylation of FRS2α and ERK1/2 and for glucose uptake.

Glucose Uptake Assay. Differentiated 3T3-L1 cells transfected with either βKlotho siRNA or control siRNA were treated with 1 μg/ml human recombinant FGF21 in DMEM supplemented with 0.1% free fatty acid (FFA)-free BSA (Sigma-Aldrich) for 18 h at 37° C. Unstimulated cells served as a negative control. The wells were washed with Krebs-Ringer-Hepes buffer supplemented with 0.1% FFA-free BSA and then incubated in the same buffer supplemented with 2-deoxy-D-[1-3H]glucose (0.4 μCi, 0.1 mM; Amersham Biosciences) for 1 h. The reaction was stopped by washing the cells twice with ice-cold PBS containing 20 μM cytochalasin B (Sigma-Aldrich) followed by snap-freezing in liquid nitrogen. Cell-associated radioactivity was determined by liquid scintillation counting. Nonspecific deoxyglucose uptake was measured in the presence of 50 μM cytochalasin B and subtracted from each sample to obtain specific uptake. A portion of each cell sample was saved immediately before the addition of D-[2-$^3$H]glucose and processed for immunoblotting with anti-βKlotho antibody, anti-GLUT1 antibody (H-43; Santa Cruz Biotechnology) and anti-GLUT4 antibody (H-61; Santa Cruz Biotechnology).

REFERENCES

1. Nishimura T. et al. (2000) *Biochim Biophys Acta* 1492:203-206.
2. Itoh N. Ornitz D M (2004) *Trends Genet* 20:563-569.
3. The ADHR Consortium (2000) *Nat Genet* 26:345-348.
4. Quarles L D (2003) *Am J Physiol* 285:E1-E9.
5. Schiavi S C, Kumar R (2004) *Kidney Int* 65:1-14.
6. Inagaki T. et al. (2005) *Cell Metab* 2:217-225.
7. Kharitonenkov A, et al. (2005) *J Clin Invest* 115:1627-1635.
8. Ibrahimi O A, et al. (2004) *Hum Mol Genet* 13:2313-2324.
9. Mohammadi M, et al. (2005) *Cytokine Growth Factor Rev* 16:107-137.
10. Zhang X, et al. (2006) *J Biol Chem* 281:15694-15700.
11. Kurosu H. et al. (2006) *J Biol Chem* 281:6120-6123.
12. Urakawa I, et al. (2006) *Nature* 444:770-774.
13. Kuro-o M, et al. (1997) *Nature* 390:45-51.
14. Shimada T, et al. (2004) *J Clin Invest* 113:561-568.
15. Razzaque M S, et al. (2006) *FASEB J* 20:720-722.
16. Pessin J E, Bell G I (1992) *Annu Rev Physiol* 54:911-930.
17. Moyers J S, et al. (2007) *J Cell Physiol* 210:1-6.
18. Ito S, et al. (2000) *Mech Dev* 98: 115-119.
19. Ito S, et al. (2005) *J Clin Invest* 115:2202-2208.
20. Yu C, et al. (2000) *J Biol Chem* 275:15482-15489.
21. Plotnikov A N, et al. (2000) *Cell* 101:413-424.
22. Kurosu H, et al. (2005) *Science* 309:1829-1833.
23. Jiang Z Y, et al. (2003) *Proc Natl Acad Sci USA* 100:7569-7574.

What is claimed is:

1. A method to identify a modulator of βKlotho-dependent glucose transporter-1 (GLUT-1) upregulation that specifically modulates interaction of βKlotho and an FGFR, the method comprising steps:

contacting an agent with a βKlotho-dependent GLUT-1 assay system under conditions wherein but for the presence of the agent, the assay has a reference GLUT-1 readout;

detecting an agent-biased specific modulation of the GLUT-1 readout significantly different from the reference readout, indicating that the agent is a modulator of GLUT-1 upregulation; and determining that the agent specifically modulates the interaction of the βKlotho and the FGFR, indicating that the modulation of the GLUT-1 upregulation is βKlotho-dependent, wherein the assay system comprises cultured 3T3-L1 adipocytes, the GLUT-1 readout is glucose uptake in the adipocytes, the FGFR is FGFR1c or FGFR4, the determining step is performed by a βKlotho-FGFR binding assay, and the agent is a compound of a drug screening compound library, a putative FGF21 protein mimetic, or an antibody.

* * * * *